(12) United States Patent
Gao et al.

(10) Patent No.: US 10,802,006 B2
(45) Date of Patent: Oct. 13, 2020

(54) METHOD FOR IDENTIFYING GRAPE SEED EXTRACT AUTHENTICITY USING HPLC FINGERPRINT SPECTRUM

(71) Applicant: Chenguang Biotech Group, Co. Ltd., Handan (CN)

(72) Inventors: Wei Gao, Handan (CN); Li Zhou, Handan (CN); Qingshan Yang, Handan (CN); Lei Wang, Handan (CN); Yunhe Lian, Handan (CN)

(73) Assignee: Chenguang Biotech Group, Co. Ltd. (CN)

( * ) Notice: Subject to any disclaimer, the term of this patent is extended or adjusted under 35 U.S.C. 154(b) by 221 days.

(21) Appl. No.: 16/067,742

(22) PCT Filed: Sep. 9, 2016

(86) PCT No.: PCT/CN2016/098552
§ 371 (c)(1),
(2) Date: Jul. 2, 2018

(87) PCT Pub. No.: WO2017/113881
PCT Pub. Date: Jul. 6, 2017

(65) Prior Publication Data
US 2019/0025265 A1    Jan. 24, 2019

(30) Foreign Application Priority Data

Dec. 30, 2015    (CN) .......................... 2015 1 1022708
Mar. 28, 2016    (CN) .......................... 2016 1 0182593

(51) Int. Cl.
| | | |
|---|---|---|
| *G01N 30/86* | (2006.01) | |
| *G01N 30/06* | (2006.01) | |
| *G16C 20/20* | (2019.01) | |
| *G16C 20/70* | (2019.01) | |
| *G01N 30/02* | (2006.01) | |
| *G01N 30/88* | (2006.01) | |

(52) U.S. Cl.
CPC ......... *G01N 30/8686* (2013.01); *G01N 30/06* (2013.01); *G16C 20/20* (2019.02); *G16C 20/70* (2019.02); *G01N 2030/027* (2013.01); *G01N 2030/8831* (2013.01)

(58) Field of Classification Search
CPC ..... G01N 2030/027; G01N 2030/8831; G01N 30/06; G01N 30/8686; G16C 20/20; G16C 20/70

USPC .................................. 436/161, 174; 422/70
See application file for complete search history.

(56) References Cited

FOREIGN PATENT DOCUMENTS

| CN | 101149361 A | 3/2008 |
|---|---|---|
| CN | 101178389 A | 5/2008 |
| CN | 102087212 A | 6/2011 |
| CN | 105842359 A | 8/2016 |

OTHER PUBLICATIONS

Weber et al. Journal of Agricultural and Food Chemistry, vol. 55, 2007, pp. 148-156.*
Govindaraghavan. Fitoterapia, vol. 134, Mar. 18, 2019, pp. 389-403.*
International Search Report; dated Nov. 29, 2016 for PCT Application No. PCT/CN2016/098552.
Fuleki, Tibor, and Jorge M. Ricardo da Silva. "Catechin and procyanidin composition of seeds from grape cultivars grown in Ontario." Journal of Agricultural and Food Chemistry 45.4 (1997): 1156-1160.
Chen, Zhao-gui, Yan-hua Lu, and Dong-zhi Wei. "Determination of procyanidin B2 in grape seed extract by RP-HPLC [J]." Chinese Traditional Patent Medicine 11 (2007): 028.
Villani, Tom S., et al. "Chemical investigation of commercial grape seed derived products to assess quality and detect adulteration." Food Chemistry 170 (2015): 271-280.

* cited by examiner

*Primary Examiner* — Maureen Wallenhorst
(74) *Attorney, Agent, or Firm* — Mendelsohn Dunleavy, P.C.

(57) ABSTRACT

A method for identifying the adulteration of a pine bark extract or a peanut skin extract in a grape seed extract using HPLC fingerprint spectrums. The method includes 1) establishing HPLC fingerprint spectrums of the three extracts; 2) determining characteristic peaks of pine bark extract and peanut skin extract; 3) testing a grape seed extract sample using liquid chromatography detection to identify the adulteration of pine bark extract or peanut skin extract in the sample according to whether the chromatogram contains the characteristic peaks of pine bark extract and/or peanut skin extract, wherein the addition of more than 3% of adulterants can be accurately identified. The method has good stability and reproducibility, high efficiency, obvious identification characteristics, provides a theoretical basis for the identification of the plant sources of grape seed extracts, and is conducive to promoting the healthy development of the plant extract industry.

19 Claims, 6 Drawing Sheets

US 10,802,006 B2

METHOD FOR IDENTIFYING GRAPE SEED EXTRACT AUTHENTICITY USING HPLC FINGERPRINT SPECTRUM

CROSS-REFERENCE TO RELATED APPLICATION

The present application claims priority to the Chinese patent application with a filing number of 201511022708.8, filed on Dec. 30, 2015, the disclosure of which is incorporated herein by reference in its entirety.

The present application also claims priority of the Chinese patent application with a filing number of 201610182593.7, filed on Mar. 28, 2016, the disclosure of which is incorporated herein by reference in its entirety.

TECHNICAL FIELD

The present invention relates to a method for identifying natural extracts using liquid chromatography technology, in particular to a method for identifying grape seed extract authenticity using HPLC fingerprint spectrum.

BACKGROUND ART

Grape Seed Extract (GSE) is a type of polyphenols extracted from grape seeds. Because of its strong antioxidant activity, it can effectively remove excess free radicals in the human body and play a role in delaying aging and enhancing immunity, and has been widely used in the industries such as food, medicine, health care products, cosmetics and the like.

The active ingredient having antioxidant effect in grape seed extract is proanthocyanidins. Its antioxidant activity and the ability of removing free radicals in the human body is 50 times greater than that of vitamin E, and 20 times greater than that of vitamin C, and proanthocyanidins has the functions of cardiovascular protection, prevention of hypertension, anti-tumor, and radiation resistance and the like. Proanthocyanidins is a mixture composed of monomers including catechin, epicatechin, epigallocatechin gallate and gallic acid, as well as oligomers and polymers formed through bonding of these monomers via C4-C6 and C4-C8 bonds and the like. Usually, dimer to tetramer are called oligomeric proanthocyanidins (OPC), and polymers with a degree of polymerization higher than that of tetramer are called polymeric proanthocyanidins (PPC), wherein the procyanidin oligomers have the strongest antioxidant activity.

A variety of plant extracts contain proanthocyanidins, but the proanthocyanidin content in different extracts varies greatly; the composition and structure of proanthocyanidins are also different, and their antioxidant effects are also different. Studies found that proanthocyanidins extracted from grape seeds are of higher purity, better quality, and stronger efficacy. At present, researches on grape seed extracts mainly focus on the detection of proanthocyanidins, but it is impossible to detect whether other extracts are adulterated into the grape seed extract. Due to the different efficacy of plant extracts from different sources, adulteration behavior is extremely harmful to the products. Therefore, it is of great significance to develop a simple and rapid adulteration detection method for grape seed extract.

The main components of pine bark extract and peanut skin extract are proanthocyanidins which are the same as that of grape seed extract, and their price is lower. Driven by profit, unscrupulous traders incorporate pine bark extract and peanut skin extract into grape seed extract, and sold the mixture pretend to be the grape seed extract. Such behavior severely disrupts the market order of grape seed extract. Although the components of pine bark extract and peanut skin extract are similar to that of grape seed extract, their efficacy and quality are different from that of grape seed extract. Their incorporation into grape seed extract will affect the efficacy of the product and seriously infringe on consumer's rights. Since pine bark extract, peanut skin extract and grape seed extract have the same main components, it is difficult to perform adulteration identification by content determination. Therefore, the authenticity identification of grape seed extract in the industry is still blank.

SUMMARY OF THE INVENTION

The object of the present invention is to provide a method for identifying grape seed extract authenticity using HPLC fingerprint spectrum, so as to identify whether the grape seed extract is adulterated with other extracts. The method can identify grape seed extract authenticity according to different HPLC spectrums of plant extracts from different sources.

In order to achieve the object of the present invention, the method for identifying grape seed extract authenticity using HPLC fingerprint spectrum comprises detecting adulterants of pine bark extract and peanut skin extract, and an authentic grape seed extract respectively, so as to find the characteristic peaks of the adulterants, and performing verification by detecting a large number of samples from different sources. The method includes the following steps:

S1: establishing HPLC fingerprint spectrums of a grape seed extract, an adulterant pine bark extract and an adulterant peanut skin extract, respectively;

S2: comparing the HPLC fingerprint spectrum of the pine bark extract with the HPLC fingerprint spectrum of the grape seed extract to determine the characteristic peak of the pine bark extract; and comparing the HPLC fingerprint spectrum of the peanut skin extract with the HPLC fingerprint spectrum of the grape seed extract to determine the characteristic peak of the peanut skin extract;

S3: determining a grape seed extract sample to be tested using high performance liquid chromatography, and identifying the adulteration of the pine bark extract or the peanut skin extract in the sample to be tested according to the presence or absence of characteristic peaks.

The specific method of S1 is as follows:

S11: preparation of a test solution: accurately weighing appropriate amounts of standard substances of grape seed extract, pine bark extract, and peanut skin extract, respectively, adding aqueous ethanol solution, performing ultrasonic dissolving, cooling and diluting to a fixed volume, so as to prepare a test solution with a concentration of 5 to 20 mg/mL; and S12: HPLC determination: respectively, accurately drawing the test solution of grape seed extract, the test solution of pine bark extract and the test solution of peanut skin extract, injecting the test solutions into a liquid chromatograph, performing detection using liquid chromatography, and respectively establishing a HPLC fingerprint spectrum of the grape seed extract, a HPLC fingerprint spectrum of the pine bark extract, and a HPLC fingerprint spectrum of the peanut skin extract with a time period of 0 to 30 min.

HPLC chromatographic conditions are as follows: octadecylsilane bonded silica gel column is used as the stationary phase, and acetonitrile and formic acid aqueous solution are used as the mobile phase for gradient elution; the flow rate is 1.2 mL/min; the detection wavelength is 270 to 310 nm (preferably 278 nm); and the temperature of the chromatographic column is 25 to 40° C. The injection volume is 5 μL.

The concentration of the aqueous ethanol solution in S11 is 20 to 80 v/v %. The ultrasonic conditions in S11 are as follows: the ultrasonic power is 600 W, the frequency is 40 KHz, and the ultrasonic time is 2 to 5 minutes, wherein the ultrasonic is started for 2 to 3 seconds, and stopped for 3 to 5 seconds.

The conditions for gradient elution in S12 are as follows: 0 to 15 min: 10% to 18% acetonitrile; 15 to 23 min: 18% to 60% acetonitrile; 23 to 24 min: 60% to 10% acetonitrile; and 24 to 30 min: 10% acetonitrile.

The specifications of the silica gel column in S12 are as follow: a length of 150 mm, an inner diameter of 4.6 mm, and a particle size of 5 μm for an octadecylsilane bonded silica gel layer.

The volumetric ratio of formic acid to water in the formic acid aqueous solution in S12 is 0.1:100.

In the aforementioned method, the HPLC fingerprint spectrum of pine bark extract is compared with the HPLC fingerprint spectrum of grape seed extract in S2, and a characteristic peak PB1 of pine bark extract is determined at 10 to 15 min, and the retention time of the characteristic peak PB1 is 11.7±1 min.

In the aforementioned method, the HPLC fingerprint spectrum of peanut skin extract is compared with the HPLC fingerprint spectrum of grape seed extract in S2, and characteristic peaks PS1 and PS2 of peanut skin extract are determined at 10 to 15 min, and retention times of the characteristic peaks PS1 and PS2 are 11.5±1 min and 11.7±1 min, respectively.

The aforementioned method, the specific process for S3 is as follows: if a peak occurs at 11.7±1 min, indicating that the sample to be tested is adulterated with pine bark extract; if peaks occur both at 11.5±1 min and 11.7±1 min, indicating that the sample to be tested is adulterated with peanut skin extract or with both peanut husk extract and pine bark extract.

The high performance liquid chromatography determination method in the present invention is described in USP 38 "Grape Seeds Oligomeric Proanthocyanidins", and the instrument conditions adopted and the like refer to the specific detection procedures and Examples. An Agilent 1260 high performance liquid chromatograph and a Zorbax SB-C18 chromatographic column are used.

The detection of the grape seed extract from different sources by using the method of the present invention results in HPLC fingerprint spectrums that are consistent in the shape, and the detection of the adulterant extracts from different sources by using the method of the present invention results in obvious characteristic peaks, which indicates that the method has a high specificity.

The method of the present invention is suitable for identifying grape seed extracts and adulterants from different sources, and has the advantages of simple operation, rapid and accurate analysis, easy identification of authenticity, and clear and explicit judgment indexes.

The method can be used for detecting whether grape seed extract is adulterated with other extracts, has good specificity and high sensitivity, and the grape seed extract adulterated with more than 3% of adulterants can be detected and identified by the method.

The method has good stability and reproducibility, is highly efficient, and has obvious identification characteristics. It provides a certain theoretical basis for identifying the plant sources of grape seed extract and is beneficial to the healthy development of the plant extract industry.

SPECIFIC MODES FOR CARRYING OUT THE EMBODIMENTS

Figure 1:
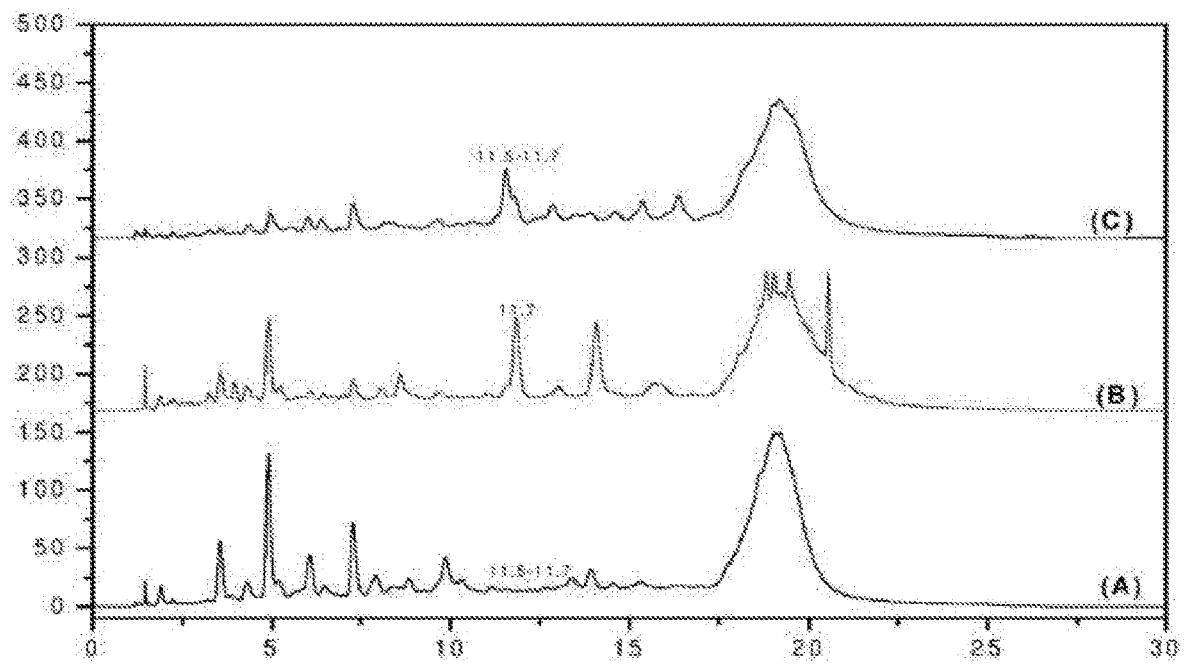
FIG. 1 shows the HPLC fingerprint spectrum established in Example 1 of the present invention; wherein, A represents grape seed extract, B represents pine bark extract, and C represents peanut skin extract.
Figure 2:
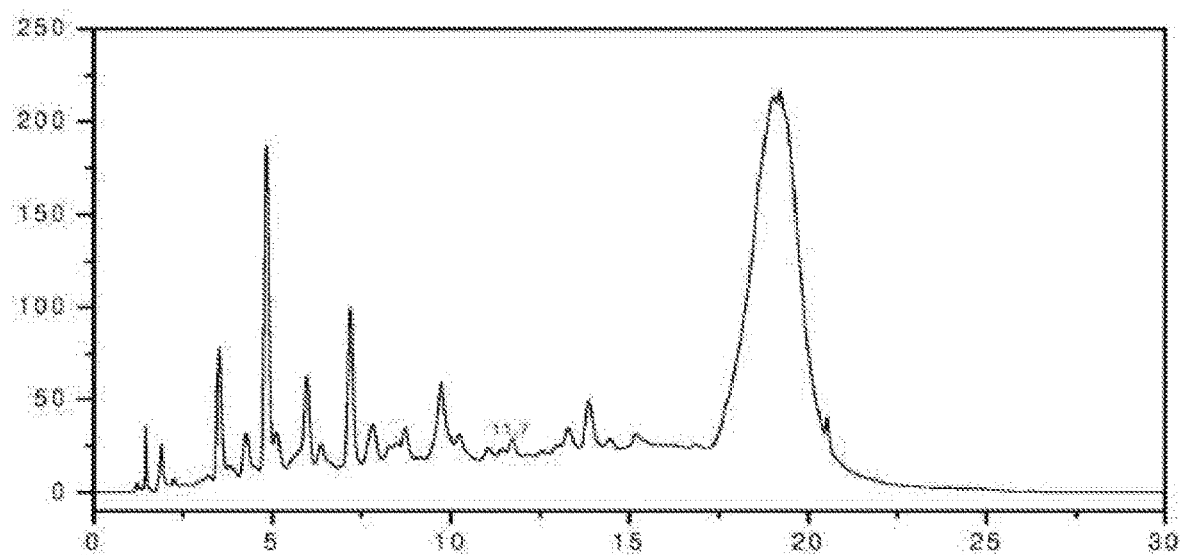
FIGS. 2-5 shows the HPLC chromatograms of grape seed extracts adulterated with 3%, 10%, 15% and 20% pine bark extract in Example 2 of the present invention, respectively.
Figure 3:
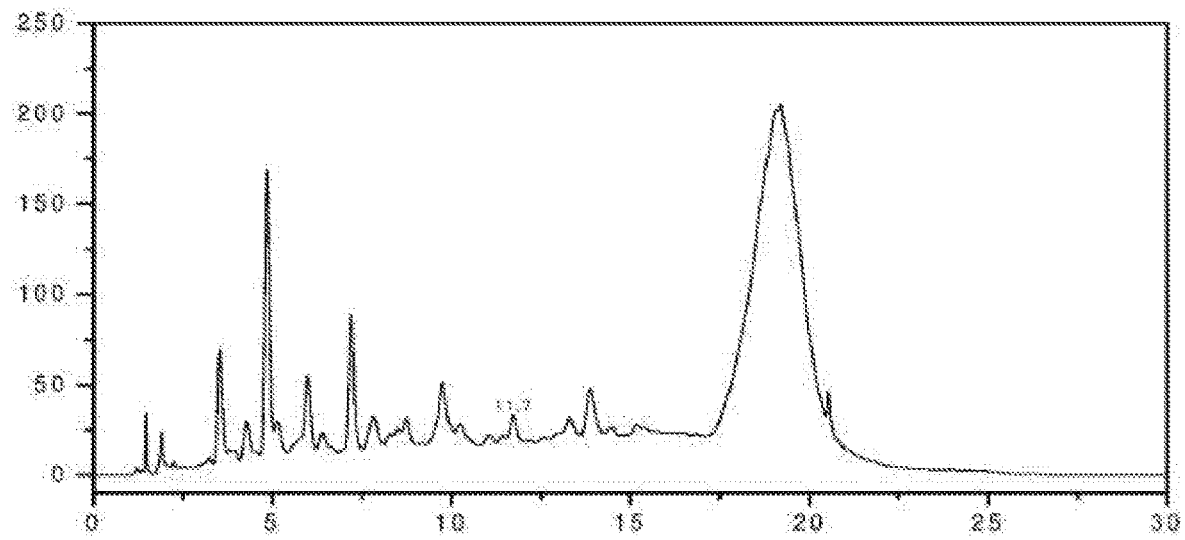
Figure 4:
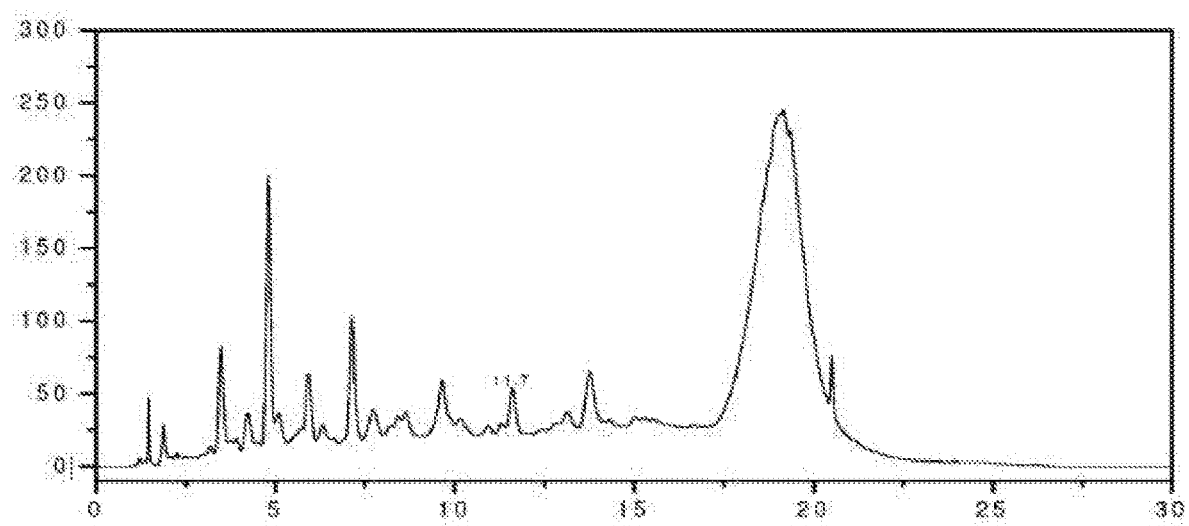
Figure 5:
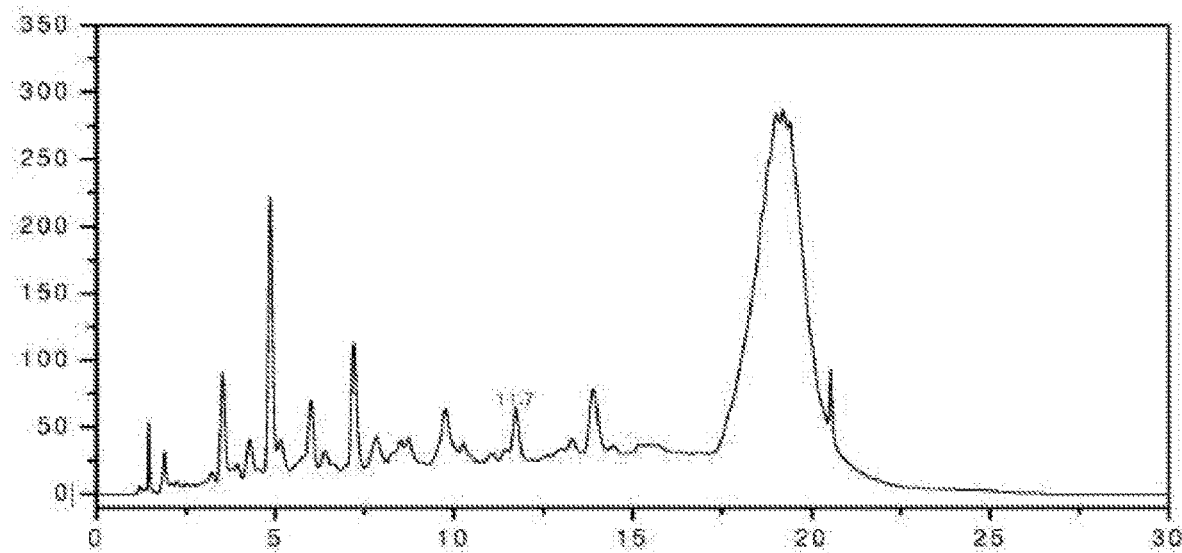
Figure 6:
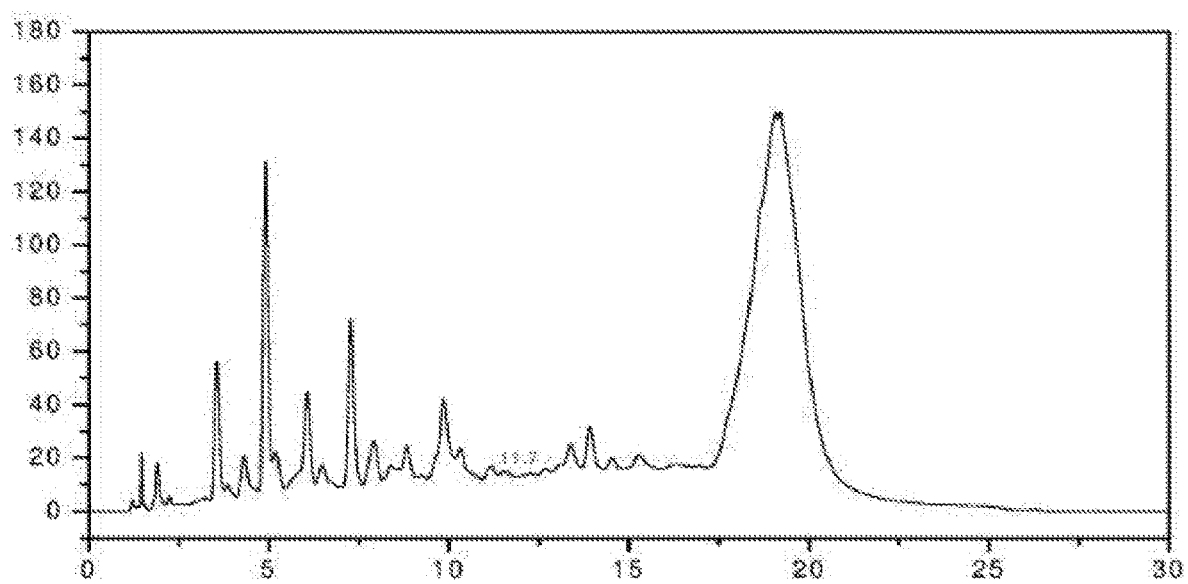
FIG. 6 shows the HPLC chromatogram of unadulterated grape seed extract in Example 2 of the present invention.
Figure 7:
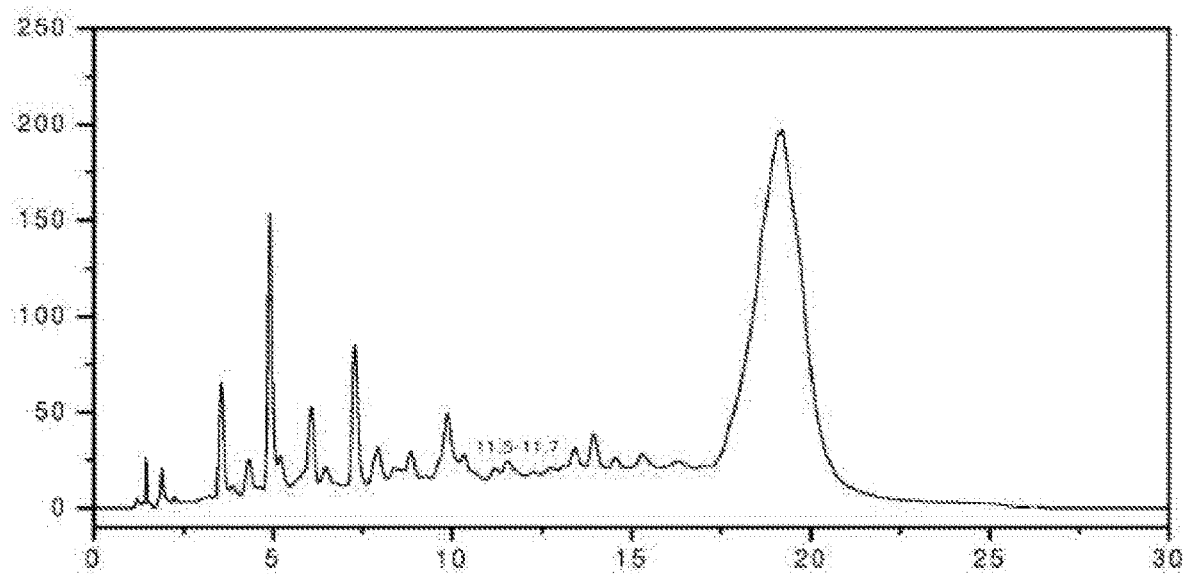
FIGS. 7-10 shows the HPLC chromatograms of grape seed extracts adulterated with 3%, 10%, 15% and 20% peanut skin extracts in Example 3 of the present invention, respectively.
Figure 8:
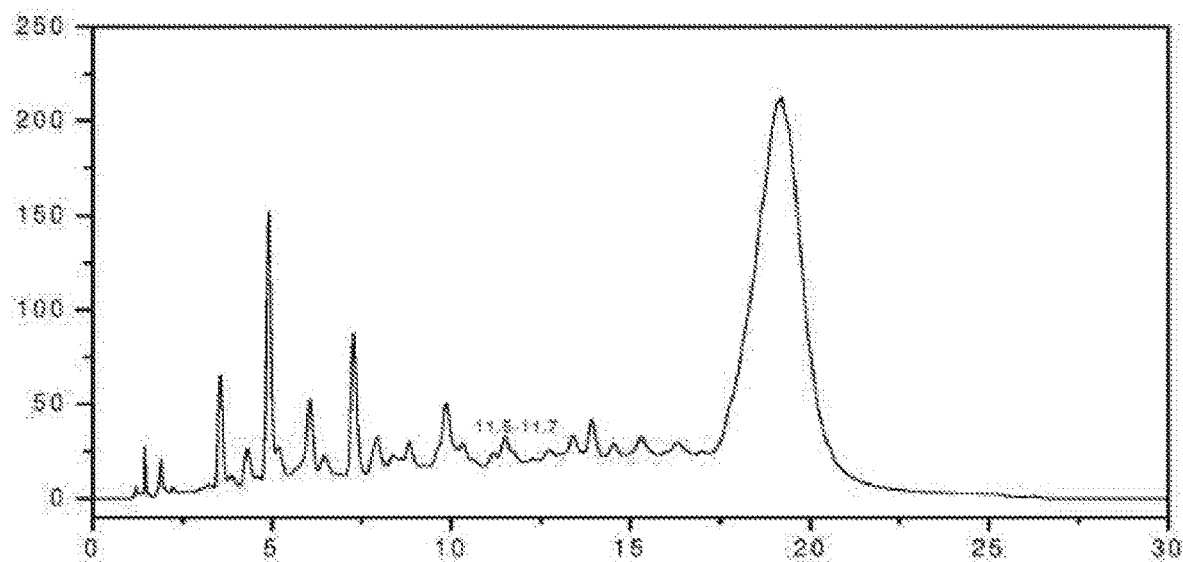
Figure 9:
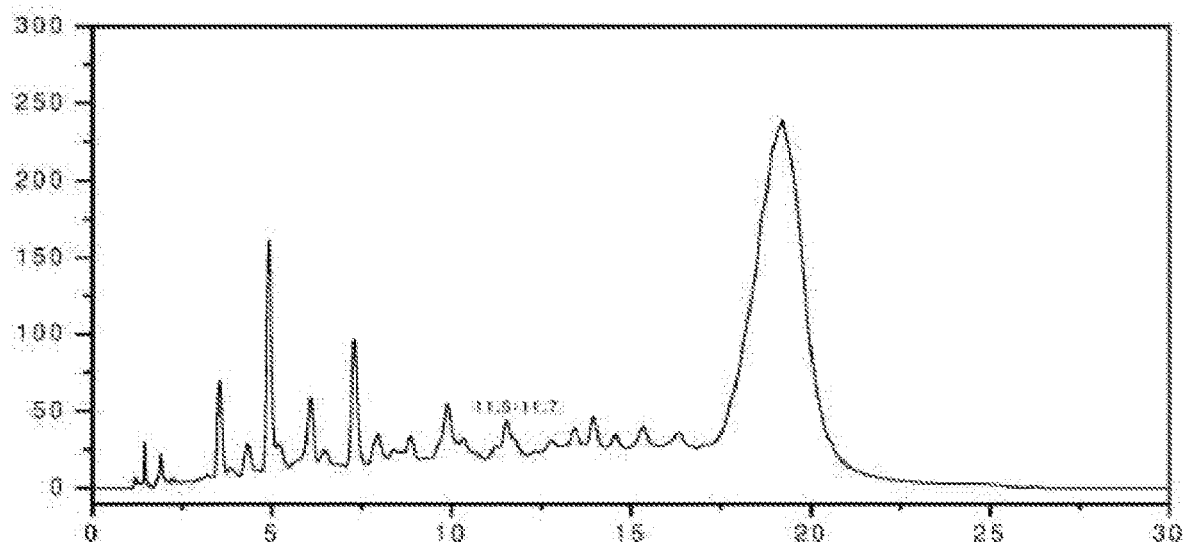
Figure 10:
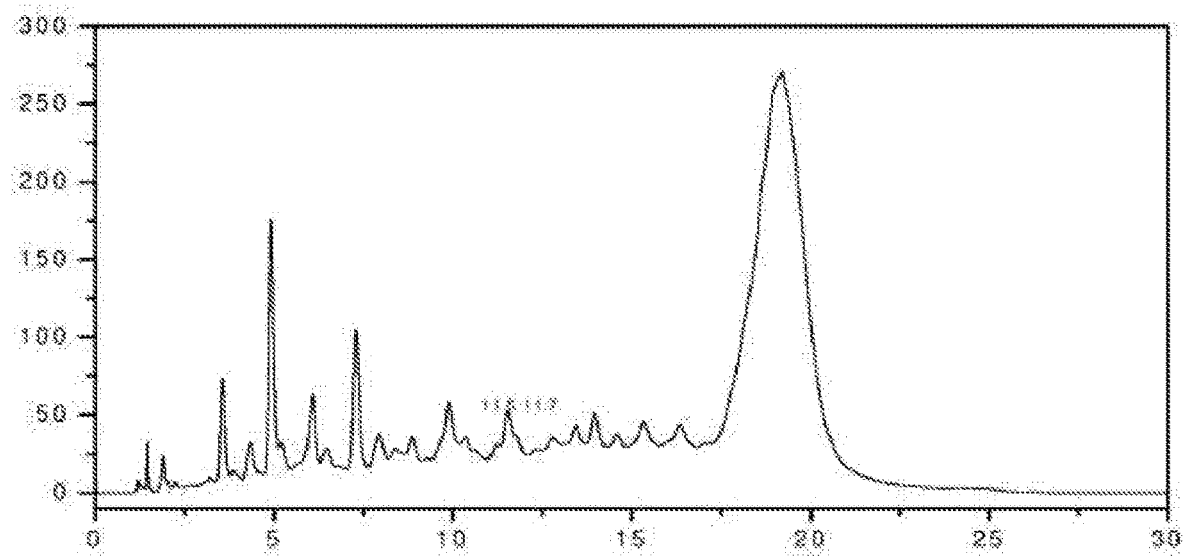
Figure 11:
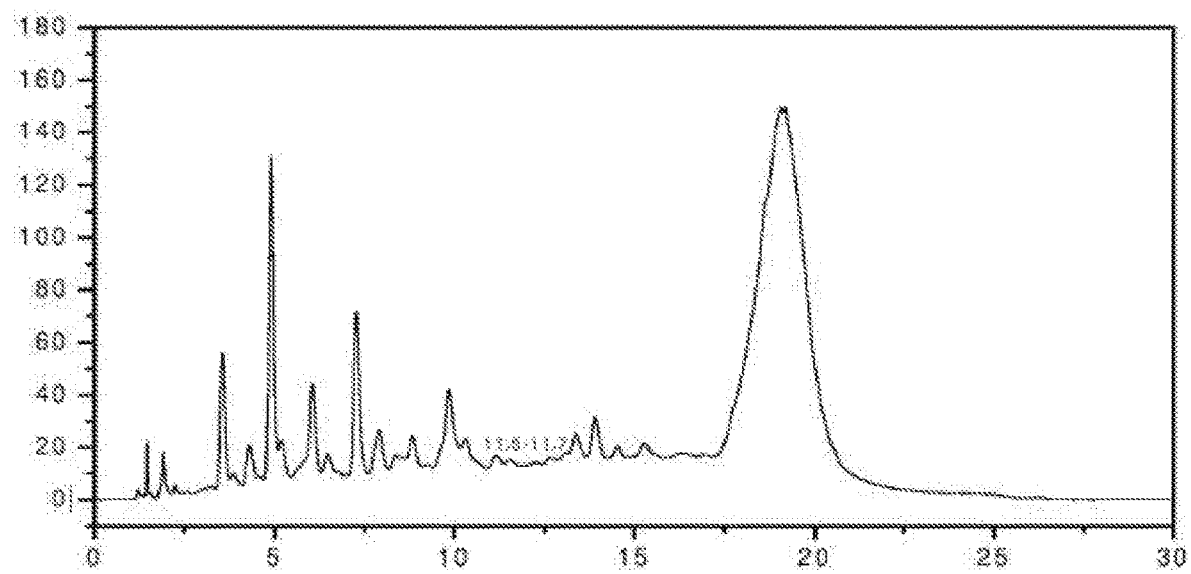
FIG. 11 shows the HPLC chromatogram of unadulterated grape seed extract in Example 3 of the present invention.

The following Examples are intended to illustrate the present invention, but are not intended to limit the scope of the present invention. Unless otherwise specified, the technical means used in the Examples are conventional means well known to a person skilled in the art, and the raw materials are all commercially available products.

Example 1: Establishment of HPLC Fingerprint Spectrums of Grape Seed Extract, Pine Bark Extract and Peanut Skin Extract 1, Instruments and Reagents
1.1 Instruments
Agilent 1260 high performance liquid chromatograph, and Zorbax SB-C18 chromatographic column (5 μm, 150 mm×4.6 mm).
1.2 Reagents
Ethanol used for extraction was an analytically pure reagent; and acetonitrile used as a reagent for the liquid phase analysis was a chromatographically pure reagent. Grape seed extract, pine bark extract, and peanut skin extract were provided by Chenguang Biotech Group Co., Ltd.
2. Methods and Results
For the separation conditions of liquid chromatography, see USP 38, Grape Seeds Oligomeric Proanthocyanidins, and the chromatographic conditions were as follows:
(1) The stationary phase was an octadecylsilane bonded silica gel column (150 mm×4.6 mm, 5 μm);
(2) The mobile phase was (A) acetonitrile, (B) water/formic acid (100/0.1, v/v); and the gradient of the mobile phase was as follows: 0-15 min: 10 to 18% A; 15-23 min: 18 to 60% A; 23-24 min: 60 to 10% A; and 24-30 min: 10% A;
(3) Flow rate: 1.2 mL/min;
(4) Detection wavelength: 278 nm; and
(5) Injection volume: 5 μL.
3. Determination of HPLC Fingerprint Spectrum
3.1 Establishment of HPLC Fingerprint Spectrum of Grape Seed Extract
(a) Preparation of a test solution: an appropriate amount of the grape seed extract standard was accurately weighed, and added into a aqueous ethanol solution with a certain volume fraction of ethanol, subjected to ultrasonic dissolving and cooling, and then the obtained solution was diluted to a fixed volume so as to prepare the test solution with a concentration of 10 mg/mL; and the ultrasonic conditions were as follows: the ultrasonic power was 600 W; the frequency was 40 KHz; the ultrasonic time was 2 to 5 minutes, wherein the ultrasonic is started for 2 to 3 seconds, and stopped for 3 to 5 seconds.

(b) The chromatographic conditions were as follows: octadecylsilane bonded silica gel was used as the stationary phase; gradient elution was performed by using acetonitrile and formic acid aqueous solution; the flow rate was 1.2 mL/min; the detection wavelength was 278 nm; and the temperature of the chromatographic column was 40° C.

(c) Measurement: the test solution of the grape seed extract was accurately drawn, and injected into a liquid chromatograph, and determined by liquid chromatography, so as to obtain a HPLC fingerprint spectrum of the grape seed extract (FIG. 1A).

3.2 Establishment of HPLC Fingerprint spectrum of Pine Bark Extract

The HPLC fingerprint spectrum of pine bark extract was establish by the same method in 3.1 (a) to (c).

3.3 Establishment of HPLC Fingerprint Spectrum of Peanut Skin Extract

The HPLC fingerprint spectrum of peanut skin extract was established by the same method in 3.1 (a) to (c).

4. Determination of the Characteristic Peaks 4.1 Determination of a Characteristic Peak PB1 of Pine Bark Extract It was determined that a peak appearing at 11.7 min±1 min was peculiar to pine bark extract by comparing the fingerprint spectrum of the grape seed extract with the fingerprint spectrum of the pine bark extract (FIG. 1B), whereas the grape seed extract showed no chromatographic peak at this retention time.

4.2 Determination of characteristic peaks PS1 and PS2 of peanut skin extract

It was determined that the peaks at 11.5 min±1 min and 11.7 min±1 min were peculiar to peanut skin extract by comparing the fingerprint spectrum of the grape seed extract with the fingerprint spectrum of the peanut skin extract (FIG. 1C), whereas the grape seed extract showed no chromatographic peak at these retention times.

Example 2: Identification of Grape Seed Extract Samples Adulterated with Pine Bark Extract The identification includes the following steps:

Step (1): the fingerprint spectrum of the grape seed extract and a fingerprint spectrum of the pine bark extract were established by the same method as in 3.1 and 3.2 of Example 1.

Step (2): the grape seed extract was adulterated with pine bark extract, and subjected to relevant detection. Homemade grape seed extract was weighed as 1.02 g, 1.10 g, 1.05 g, and 1.09 g, respectively; and 0.03 g, 0.1 g, 0.15 g, and 0.2 g of pine bark extracts were added respectively, i.e. the adulteration amount were 3%, 10%, 15%, and 20%, respectively. The adulterated grape seed extracts were subjected to liquid chromatography detection by the same method as in 3.1 of Example 1.

The results were shown in FIGS. 2 to 6. It can be seen from the HPLC chromatograms that, the chromatograms of the extracts adulterated with pine bark extract had a significant chromatographic peak at about 11.7 min±1 min, while the grape seed extract without pine bark extract had no obvious chromatographic peak at this time point, and the characteristic peak increased as the proportion of the added pine bark extract increased.

Example 3: Identification of Grape Seed Extract Samples Adulterated with Peanut Skin Extract The identification included the following steps:

Step (1): a fingerprint spectrum of the grape seed extract and a fingerprint spectrum of the peanut skin extract were established by the same methods as in 3.1 and 3.3 of Example 1.

Step (2): the grape seed extract was adulterated with peanut skin extract, and subjected to relevant detection. Homemade grape seed extract was weighed as 1.01 g, 1.0.5 g, 1.08 g, and 1.09 g, respectively; and 0.03 g, 0.1 g, 0.15 g, and 0.2 g of peanut skin extract were added respectively, i.e. the adulteration amount were 3%, 10%, 15%, and 20%, respectively. The adulterated grape seed extracts were subjected to liquid chromatography detection by the same method as in 3.1 of Example 1.

The results were shown in FIGS. 7 to 11. It can be seen from the HPLC chromatograms that, the chromatograms of the extracts adulterated with pine bark extract had significant chromatographic peaks at about 11.5 min±1 min and 11.7 min±1 min, while the grape seed extract without pine bark extract had no obvious chromatographic peak at 11.5 min±1 min or 11.7 min±1 min, and the characteristic peaks increased as the proportion of the added peanut skin extract increased.

Although the present invention has been described above in detail with general description and specific embodiments, it is obvious to a person skilled in the art that some modifications or improvements can be made on the basis of the present invention. Therefore, these modifications or improvements made without departing from the spirit of the present invention all fall within the protection scope of the present invention.

INDUSTRIAL APPLICABILITY

The present invention provides a method for identifying grape seed extract authenticity using an HPLC fingerprint spectrum, and in particular, provides a method for identifying whether the grape seed extract was adulterated with pine bark extract or peanut skin extract. The method has good stability and reproducibility, high efficiency, obvious identification characteristics, provides a theoretical basis for the identification of the plant sources of grape seed extracts, and is conducive to promoting the healthy development of the plant extract industry.

What is claimed is:

1. A method for identifying grape seed extract authenticity using HPLC fingerprint spectrum, wherein the method comprises:
    S1: establishing HPLC fingerprint spectrums of a grape seed extract, a pine bark extract, and a peanut skin extract, respectively;
    S2: comparing the HPLC fingerprint spectrum of the pine bark extract with the HPLC fingerprint spectrum of the grape seed extract to determine a characteristic peak of the pine bark extract and comparing the HPLC fingerprint spectrum of the peanut skin extract with the HPLC fingerprint spectrum of the grape seed extract to determine a characteristic peak of the peanut skin extract; and S3: testing a grape seed extract sample using high performance liquid chromatography to generate an HPLC test spectrum, identifying presence or absence of an adulteration of the pine bark extract in the sample according to respective presence or absence of the characteristic peak of the pine bark extract in the HPLC test spectrum, and identifying presence or absence of an adulteration of the peanut skin extract in the sample according to respective presence or absence of the characteristic peak of the peanut skin extract in the HPLC test spectrum, wherein:

the HPLC fingerprint spectrum of the pine bark extract is compared with the HPLC fingerprint spectrum of the grape seed extract in S2, a characteristic peak PB1 of the pine bark extract is determined at 10 to 15 min, and a retention time of the characteristic peak PB1 is 11.7±1 min.

2. The method according to claim 1, wherein the step S1 comprises:

S11: preparation of test solutions: accurately weighing appropriate amounts of grape seed extract, pine bark extract, and peanut skin extract, respectively, adding aqueous ethanol solution, performing ultrasonic dissolving, cooling, and diluting to a fixed volume, so as to prepare a test solution of grape seed extract, a test solution of pine bark extract, and a test solution of peanut skin extract, each with a concentration of 5 to 20 mg/mL; and S12: HPLC determination: drawing and injecting a portion of the test solution of grape seed extract into a liquid chromatograph, performing detection using liquid chromatography, and establishing the HPLC fingerprint spectrum of the grape seed extract with a time period of 0 to 30 min; drawing and injecting a portion of the test solution of pine bark extract into a liquid chromatograph, performing detection using liquid chromatography, and establishing the HPLC fingerprint spectrum of the pine bark extract with a time period of 0 to 30 min; and drawing and injecting a portion of the test solution of peanut skin extract into a liquid chromatograph, performing detection using liquid chromatography, and establishing the HPLC fingerprint spectrum of the peanut skin extract with a time period of 0 to 30 min, wherein, HPLC chromatographic conditions are as follows: octadecylsilane bonded silica gel column is used as a stationary phase, and an aqueous solution comprising acetonitrile and formic acid is used as a mobile phase for gradient elution; a flow rate is 1.2 mL/min; a detection wavelength is 270 to 310 nm; and a temperature of the chromatographic column is 25 to 40° C.

3. The method according to claim 2, wherein a concentration of the aqueous ethanol solution in S11 is 20 to 80 v/v %.

4. The method according to claim 3, wherein ultrasonic conditions in S11 are as follows: ultrasonic power is 600 W with a frequency of 40 KHz and an ultrasonic time of 2 to 5 minutes, wherein the ultrasonic is started for 2 to 3 seconds, and stopped for 3 to 5 seconds.

5. The method according to claim 2, wherein ultrasonic conditions in S11 are as follows: ultrasonic power is 600 W with a frequency of 40 KHz and an ultrasonic time of 2 to 5 minutes, wherein the ultrasonic is started for 2 to 3 seconds, and stopped for 3 to 5 seconds.

6. The method according to claim 5, wherein conditions for gradient elution in S12 using the aqueous solution comprising acetonitrile and formic acid are as follows: 0 to 15 min: 10% to 18% acetonitrile; 15 to 23 min: 18% to 60% acetonitrile; 23 to 24 min: 60% to 10% acetonitrile; and 24 to 30 min: 10% acetonitrile.

7. The method according to claim 2, wherein conditions for gradient elution in S12 using the aqueous solution comprising acetonitrile and formic acid are as follows: 0 to 15 min: 10% to 18% acetonitrile; 15 to 23 min: 18% to 60% acetonitrile; 23 to 24 min: 60% to 10% acetonitrile; and 24 to 30 min: 10% acetonitrile.

8. The method according to claim 7, wherein specifications of the silica gel column in S12 are as follow: a length of 150 mm, an inner diameter of 4.6 mm, and a particle size of 5 μm for an octadecylsilane bonded silica gel layer.

9. The method according to claim 2, wherein specifications of the silica gel column in S12 are as follow: a length of 150 mm, an inner diameter of 4.6 mm, and a particle size of 5 μm for an octadecylsilane bonded silica gel layer.

10. The method according to claim 9, wherein the volume ratio of formic acid to water in the formic acid aqueous solution in S12 is 0.1:100.

11. The method according to claim 2, wherein a volume ratio of formic acid to water in the aqueous solution in S12 is 0.1:100.

12. The method according to claim 2, wherein the HPLC fingerprint spectrum of the peanut skin extract is compared with the HPLC fingerprint spectrum of the grape seed extract in S2, characteristic peaks PS1 and PS2 of the peanut skin extract are determined at 10 to 15 min, and retention times of characteristic peaks PS1 and PS2 are 11.5±1 min and 11.7±1 min, respectively.

13. The method according to claim 12, wherein a concentration of the aqueous ethanol solution in S11 is 20 to 80 v/v %.

14. The method according to claim 1, wherein the HPLC fingerprint spectrum of the peanut skin extract is compared with the HPLC fingerprint spectrum of the grape seed extract in S2, characteristic peaks PS1 and PS2 of the peanut skin extract are determined at 10 to 15 min, and retention times of characteristic peaks PS1 and PS2 are 11.5±1 min and 11.7±1 min, respectively.

15. The method according to claim 14, wherein the step S3 comprises: if a peak occurs in the HPLC test spectrum at 11.7±1 min, then determining that the sample is adulterated with the pine bark extract; and if peaks occur in the HPLC test spectrum both at 11.5±1 min and 11.7±1 min, then determining that the sample is adulterated with the peanut skin extract or with both the peanut skin extract and the pine bark extract.

16. The method according to claim 1, wherein the step S3 comprises: if a peak occurs in the HPLC test spectrum at 11.7±1 min, then determining that the sample is adulterated with the pine bark extract; and if peaks occur in the HPLC test spectrum both at 11.5±1 min and 11.7±1 min, then determining that the sample is adulterated with the peanut skin extract or with both the peanut skin extract and the pine bark extract.

17. A method for identifying grape seed extract authenticity using HPLC fingerprint spectrum, wherein the method comprises:

S1: establishing HPLC fingerprint spectrums of a grape seed extract, a pine bark extract, and a peanut skin extract, respectively;

S2: comparing the HPLC fingerprint spectrum of the pine bark extract with the HPLC fingerprint spectrum of the grape seed extract to determine a characteristic peak of the pine bark extract and comparing the HPLC fingerprint spectrum of the peanut skin extract with the HPLC fingerprint spectrum of the grape seed extract to determine a characteristic peak of the peanut skin extract; and S3: testing a grape seed extract sample using high performance liquid chromatography to generate an HPLC test spectrum, identifying presence or absence of an adulteration of the pine bark extract in the sample according to respective presence or absence of the characteristic peak of the pine bark extract in the HPLC test spectrum, and identifying presence or absence of an adulteration of the peanut skin extract in the sample according to respective presence or absence of the characteristic peak of the peanut skin extract in the HPLC test spectrum, wherein:

the HPLC fingerprint spectrum of the peanut skin extract is compared with the HPLC fingerprint spectrum of the grape seed extract in S2, characteristic peaks PS1 and PS2 of the peanut skin extract are determined at 10 to 15 min, and retention times of characteristic peaks PS1 and PS2 are 11.5±1 min and 11.7±1 min, respectively.

18. The method according to claim 17, wherein the step S3 comprises: if a peak occurs in the HPLC test spectrum at 11.7±1 min, then determining that the sample is adulterated with the pine bark extract; and if peaks occur in the HPLC test spectrum both at 11.5±1 min and 11.7±1 min, then determining that the sample is adulterated with the peanut skin extract or with both the peanut skin extract and the pine bark extract.

19. A method for identifying grape seed extract authenticity using HPLC fingerprint spectrum, wherein the method comprises the following steps:

S1: establishing HPLC fingerprint spectrums of a grape seed extract, a pine bark extract, and a peanut skin extract, respectively;

S2: comparing the HPLC fingerprint spectrum of the pine bark extract with the HPLC fingerprint spectrum of the grape seed extract to determine a characteristic peak of the pine bark extract and comparing the HPLC fingerprint spectrum of the peanut skin extract with the HPLC fingerprint spectrum of the grape seed extract to determine a characteristic peak of the peanut skin extract; and S3: testing a grape seed extract sample using high performance liquid chromatography to generate an HPLC test spectrum, identifying presence or absence of an adulteration of the pine bark extract in the sample according to respective presence or absence of the characteristic peak of the pine bark extract in the HPLC test spectrum, and identifying presence or absence of an adulteration of the peanut skin extract in the sample according to respective presence or absence of the characteristic peak of the peanut skin extract in the HPLC test spectrum, wherein:

the step of S3 comprises: if a peak occurs in the HPLC test spectrum at 11.7±1 min, then determining that the sample is adulterated with the pine bark extract; and if peaks occur in the HPLC test spectrum both at 11.5±1 min and 11.7±1 min, then determining that the sample is adulterated with the peanut skin extract or with both the peanut skin extract and the pine bark extract.

\* \* \* \* \*